United States Patent
Jain et al.

(10) Patent No.: US 12,175,680 B2
(45) Date of Patent: Dec. 24, 2024

(54) SYSTEM AND METHOD FOR MONITORING HEALTH OF LOW-COST SENSORS USED IN SOIL MOISTURE MEASUREMENT

(71) Applicant: Tata Consultancy Services Limited, Mumbai (IN)

(72) Inventors: Prachin Lalit Jain, Thane West (IN); Swagatam Bose Choudhury, Thane West (IN); Prakruti Vinodchandra Bhatt, Thane West (IN); Sanat Sarangi, Thane West (IN); Srinivasu Pappula, Thane West (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 91 days.

(21) Appl. No.: 17/594,378

(22) PCT Filed: Nov. 19, 2020

(86) PCT No.: PCT/IN2020/050971
§ 371 (c)(1),
(2) Date: Oct. 13, 2021

(87) PCT Pub. No.: WO2021/144807
PCT Pub. Date: Jul. 22, 2021

(65) Prior Publication Data
US 2022/0349838 A1 Nov. 3, 2022

(30) Foreign Application Priority Data
Jan. 13, 2020 (IN) .............................. 202021001465

(51) Int. Cl.
*G06T 7/136* (2017.01)
*G01N 21/88* (2006.01)
(Continued)

(52) U.S. Cl.
CPC ....... *G06T 7/136* (2017.01); *G01N 21/95684* (2013.01); *G01N 33/246* (2013.01);
(Continued)

(58) Field of Classification Search
CPC ......... A01B 79/005; G01N 2021/8887; G01N 21/95684; G01N 33/246; G06Q 10/0639;
(Continued)

(56) References Cited

U.S. PATENT DOCUMENTS 7,170,302 B2  1/2007  Lee
9,251,698 B2  2/2016  Vian et al.
(Continued)

FOREIGN PATENT DOCUMENTS

WO  WO2015/195746 A1  12/2015
WO  WO2016/130804 A1  8/2016

OTHER PUBLICATIONS

Suzuki, Satoshi, and Keiichi Abe. "Topological structural analysis of digitized binary images by border following." Computer Vision, Graphics, and Image Processing, vol. 29, No. 3, 1985, p. 396, https://doi.org/10.1016/0734-189x(85)90136-7. (Year: 1985).*

(Continued)

*Primary Examiner* — Lisa M Caputo
*Assistant Examiner* — Joshua L Forristall
(74) *Attorney, Agent, or Firm* — FINNEGAN, HENDERSON, FARABOW, GARRETT & DUNNER LLP

(57) ABSTRACT

This disclosure relates generally to a system and method for monitoring performance of low-cost sensors plied in a field for soil moisture measurement. The low-cost sensors are calibrated to give useful derived parameters to support farming such as volumetric water content (VWC) of the soil. Further, the steps are being incorporated to de-noise their response to derive stable measurements similar to expensive (Continued)

rugged sensors. The calibration of the low-cost sensor and normalization of incoming values from the low-cost sensor are based on values determined through rugged sensors for soil moisture measurement. The normalization involves finding a minimum value and maximum value of soil moisture. Performance of the low-cost sensors are analyzed based on a range of values of the soil moisture. Finally, the performance analysis provides degradation stages and based on the degradation stages evaluated recommendations to modify the sensor are shared with the user.

11 Claims, 4 Drawing Sheets

(51) Int. Cl.
| | | |
|---|---|---|
| G01N 21/956 | (2006.01) | |
| G01N 33/24 | (2006.01) | |
| G06T 7/12 | (2017.01) | |
| G06V 10/30 | (2022.01) | |
| G06V 10/44 | (2022.01) | |

(52) U.S. Cl.
CPC ............... *G06T 7/12* (2017.01); *G06V 10/30* (2022.01); *G06V 10/44* (2022.01); *G01N 2021/8887* (2013.01); *G06T 2207/20028* (2013.01)

(58) Field of Classification Search
CPC ............... G06Q 10/20; G06Q 50/02; G06T 2207/20028; G06T 2207/20192; G06T 7/0004; G06T 7/12; G06T 7/136; G06T 7/10; G06V 10/30; G06V 10/44
USPC .......................................................... 702/104
See application file for complete search history.

(56) References Cited

U.S. PATENT DOCUMENTS

| | | | |
|---|---|---|---|
| 9,585,307 | B2 | 3/2017 | Holland |
| 10,371,637 | B1* | 8/2019 | Jaster ........................ G01V 8/10 |
| 10,670,763 | B2 | 6/2020 | Rhodes et al. |
| 2013/0058560 | A1* | 3/2013 | Sobczak ................... G06T 7/62 |
| | | | 382/152 |
| 2019/0339685 | A1 | 11/2019 | Cella et al. |
| 2020/0387419 | A1* | 12/2020 | Yang ................... G06F 11/0709 |

OTHER PUBLICATIONS

International Search Report and Written Opinion mailed May 21, 2021, in International Application No. PCT/IN2020/50971; 7 pages.

* cited by examiner

SYSTEM AND METHOD FOR MONITORING HEALTH OF LOW-COST SENSORS USED IN SOIL MOISTURE MEASUREMENT

CROSS-REFERENCE TO RELATED APPLICATIONS AND PRIORITY

This application is a U.S. National Stage Filing under 35 U.S.C. § 371 and claims priority from International Application No. PCT/IN2020/050971, filed on Nov. 19, 2020, which application claims priority under 35 U.S.C. § 119 from Indian Application No. 202021001465, filed on Jan. 13, 2020. The entire contents of the aforementioned applications are incorporated herein by reference.

TECHNICAL FIELD

The disclosure herein generally relates to a field of monitoring health of sensors used in soil moisture measurement and, more particularly, a system and method for monitoring health of low-cost sensors used in soil moisture measurement.

BACKGROUND

As a general practice, a farmer irrigates the land with lot of water, until the entire farm is flooded as he is unaware about the actual amount of water required by the soil. Surplus water is wasted and sometimes plants are also destroyed. To measure the right amount of moisture in the soil, a soil moisture sensor is used. The soil moisture sensor provides insight and helps the farmer to know the precise amount of water required and in turn preserve water.

Rugged soil moisture sensors with stable measurement profiles are usually expensive for a common farmer. The moisture readings for frugal, inexpensive, and often resistive sensors are usually jittery, where the sensor health tends to degrade over a period. Failing to catch the reduced reliability due to degraded sensor health would lead to imprecise irrigation decisions. Precision farming has an indispensable role to play in order to make this progress sustainable and its adoption at scale would require the deployments to be affordable.

Low-cost resistive/capacitive based soil moisture sensors have also been used in the prior art. The low-cost sensors usually have shorter lifetime due to faster wear and tear of the sensing element. They often give out the raw measurements with no correlation to the characteristics of the medium under observation. Once the sensors are deployed in the farm, the wear and tear of the sensing element is not observed or most of the times goes unnoticed. This leads to logging of incorrect sensor values and therefore incorrect estimates.

SUMMARY

Embodiments of the present disclosure present technological improvements as solutions to one or more of the above-mentioned technical problems recognized by the inventors in conventional systems. For example, in one embodiment, a method to monitor performance of low-cost sensors which are used in soil moisture measurement is provided.

In one aspect, a processor-implemented method to monitor performance of low-cost sensors which are used in soil moisture measurement. Herein, the low-cost sensors are calibrated to give useful derived parameters to support farming such as volumetric water content (VWC) of the soil. Further, the steps are being incorporated to de-noise their response to derive stable measurements similar to expensive rugged sensors.

The method comprises one or more steps as follows. Herein, at least one low-cost sensor is considered to measure soil moisture of a field. It is to be noted that the low-cost sensor works on a principle of resistance or capacitance through one or more sensing element. The considered low-cost sensor is calibrated based on predefined parameters to achieve one or more values of the soil moisture. The calibration of the low-cost sensor includes normalization of incoming values from the low-cost sensor based on the predefined values determined through a rugged sensor for soil moisture measurement. The normalization of the incoming values is a process of mapping of raw values, which changes even between the sensing elements of the same family to a percentage value based on air and water measurement.

Further, the method comprises performance analysis of the low-cost sensor using the achieved one or more values of the soil moisture. The performance analysis includes evaluation of degradation stages of the low-cost sensor. Finally, recommending one or more corrective measures for the low-cost sensors based on the performance analysis output. The one or more corrective measures include modifications within the existing low-cost sensor or replacement with a new low-cost sensor. Herein, the performance analysis comprises image processing of an image having the low-cost sensor to locate a base and at least one probe of the sensor, segmenting of pixels of the received image corresponding to each sensing element on the at least one probe, quantifying the sensing element on the at least one probe and checking connectivity of the sensing element on the at least one probe with the base of the low-cost sensor.

In another aspect, a system is configured to monitor performance of low-cost sensors, which are used in soil moisture measurement. The system comprising at least one memory storing a plurality of instructions and one or more hardware processors communicatively coupled with at least one memory. The one or more hardware processors are configured to execute one or more modules comprises of a calibration module, an analyzing module, and a recommendation module. Further, the system comprises at least one low-cost sensor, which works on a principle of resistance and capacitance through its sensing elements.

The calibration module of the system is configured to calibrate the low-cost sensor based on predefined parameters to achieve one or more values of the soil moisture. It is to be noted that the calibration of the low-cost sensor includes normalization of incoming values from the low-cost sensor based on predefined values determined through a rugged sensor for soil moisture measurement. Further, the normalization involves finding a minimum value and maximum value of the soil moisture. The analyzing module of the system configured to analyze performance of the low-cost sensor based on a predefined range of values of the soil moisture. The performance analysis includes evaluation of degradation stages of the low-s cost sensor. The recommendation module of the system is configured to recommend one or more corrective measures based on the performance analysis output. The one or more corrective measures include modification in the existing low-cost sensor or a replacement with a new low-cost sensor.

In yet another embodiment, a non-transitory computer readable medium storing one or more instructions which when executed by a processor on a system to cause the processor to perform method is provided.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

Figure 1:
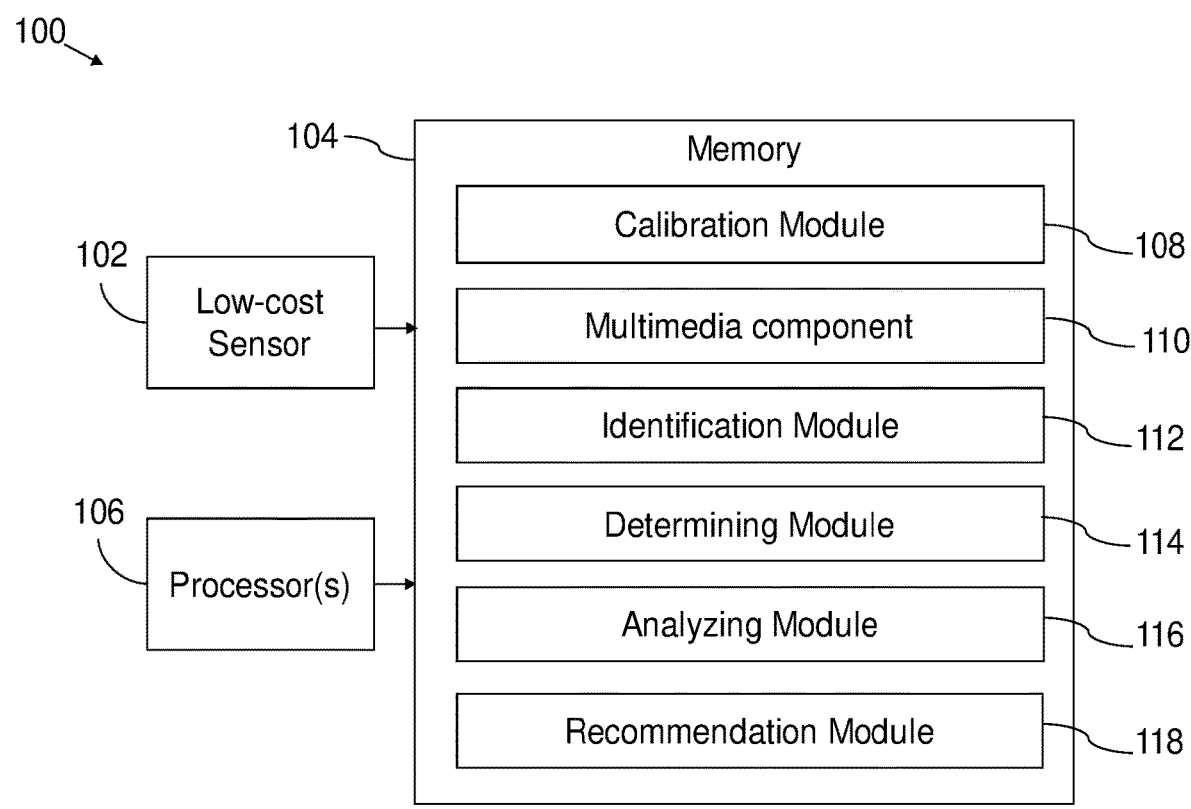
FIG. 1 illustrates a block diagram of a system to monitor performance of low-cost sensors used in soil moisture measurement, in accordance with some embodiments of the present disclosure.

It should be appreciated by those skilled in the art that any block diagrams herein represent conceptual views of illustrative systems and devices embodying the principles of the present subject matter. Similarly, it will be appreciated that any flow charts, flow diagrams, and the like represent various processes, which may be substantially represented in computer readable medium and so executed by a computer or processor, whether or not such computer or processor is explicitly shown.

DETAILED DESCRIPTION OF EMBODIMENTS

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

The embodiments herein provide a method and a system to monitor performance of low-cost sensors used in soil moisture measurement. The low-cost sensors available in the market usually have shorter lifetimes due to faster wear and tear of the sensing element. They often give out the raw measurements that are a function of the both the medium and the quality of the sensing element in contact with the medium. Once the low-cost sensors are deployed in the field, wear and tear of the sensing element is not observed or most of the times goes unnoticed. This leads to logging of incorrect sensor values and it provides incorrect estimates. Therefore, a system to calibrate the low-cost sensors based on behavior of a rugged sensor as it is trained to recognize conditions ranging from dry to moist to extreme wet conditions. Further, the system is enabled to monitor performance of the low-cost sensors and recommend modifications within the existing sensors or replacement with a new sensor. It is to be noted that the term "low-cost sensor" and "first sensor" are used interchangeably. Similarly, "rugged sensor" and "second sensor" are used interchangeably.

Referring now to the drawings, and more particularly to FIG. 1 through FIG. 4, where similar reference characters denote corresponding features consistently throughout the figures, there are shown preferred embodiments and these embodiments are described in the context of the following exemplary system and/or method.

FIG. 1 illustrates a system (100) to monitor performance of low-cost sensors used in soil moisture measurement. In the preferred embodiment, the system (100) comprises at least one low-cost sensor (102), which works on either principle of resistance or capacitance. Further, the system comprises at least one memory (104) with a plurality of instructions and one or more hardware processors (106) which are communicably coupled with the at least one memory (104) to execute modules therein.

The hardware processor (106) may be implemented as one or more microprocessors, microcomputers, microcontrollers, digital signal processors, central processing units, state machines, logic circuits, and/or any devices that manipulate signals based on operational instructions. Among other capabilities, the hardware processor (106) is configured to fetch and execute computer-readable instructions stored in the memory (104). Further, the system comprises a calibration module (108), a multimedia component (110), an identification module (112), a determining module (114), an analyzing module (116), and a recommendation module (118).

In the preferred embodiment of the disclosure, the at least one low-cost sensor (102) is configured to measure soil moisture of a field. It is to be appreciated that the at least one low-cost sensor works either on a principle of resistance or capacitance through its sensing element. The at least one low-cost sensor comprises one or more nodes integrated with a plurality of wireless sensors including temperature, humidity, soil moisture, leaf wetness, lux sensor, in portable and stationary configurations that cater to various scenarios and associated challenges in sensing the farm.

The low-cost sensor is usually jittery where the performance of the sensor tends to degrade over a period. The low-cost sensor often gives out raw measurements that are a function of both a medium and a quality of the sensing element in contact with the medium. There are no derived parameters for irrigation as such. Once the low-cost sensor is deployed in the field, wear and tear of the sensing element is not observed or most of the times goes unnoticed. It is observed that the low-cost sensor does not give a steady output in a given medium, and at irregular intervals, the low-cost sensor provides abnormal outputs like sudden trough or crest. Variance between consecutive values is also high which makes it difficult to use them without some standardization.

In the preferred embodiment of the disclosure, the calibration module (108) of the system (100) is configured to calibrate the at least one low-cost sensor based on predefined parameters to achieve a value of the soil moisture. The calibration includes normalization of the incoming values from the at least one low-cost sensor to remove bias across similar such devices. The normalization of the at least one low-cost sensor involves finding the two extreme measurements except measuring moisture content in the air and when completely immersed in water.

Herein, a Support Vector Regression (SVR) model and a Random Forest (RF) based regression model are trained to calibrate the low-cost sensor in line with rugged sensors for soil moisture measurement. A predefined training dataset is used to train the SVR model to get optimum values of one or more parameters such as epsilon and cost. It would be appreciated that the cost is a regularization parameter that controls the trade-off between achieving a low training error and a low testing error. Values of epsilon defines a margin of tolerance where no penalty is given to errors. The one or more tuned parameter values are used to create a model, which would provide a least root mean square error (RMSE).

The random forest-based regression model works by constructing a multitude of decision trees at training time and outputting the mean prediction (regression) of the individual trees. It is very important to select the number of trees that the regression model needs to grow. It is to be noted that the number should not be set to too small to ensure that every input row is predicted at least a few times. Once the regression model is created, the testing dataset is used to validate the regression model and to calculate the RMSE value.

One or more values of volumetric water content (VWC) received from the low-cost sensor are used as an input to the SVR model to estimate RMSE, when compared with the one or more values of VWC from the rugged sensors positioned for soil moisture measurement. The output of the SVR model is considered as calibrated to provide values in terms of VWC.

In the preferred embodiment of the disclosure, the multimedia component (110) is configured to capture at least one image of the employed at least one low-cost sensor. The captured at least one image is pre-processed to remove noise and detect a binary edge-map of the at least one captured image. The pre-processing of the one or more image includes conversion of each of one or more images into a greyscale and blur the grey-scaled images using a bilateral filter.

In the preferred embodiment of the disclosure, the identification module (112) of the system (100) is configured to identify a contour of a probe of the at least one low-cost sensor from the pre-processed at least one image based on a topological structural analysis on the binary edge-map of the image. The identified contour of the probe provides a silver metal pixel of each probe.

In the preferred embodiment of the disclosure, the determining module (114) of the system (100) is configured to determine a percentage of the silver metal pixel and a connectivity of the silver metal pixel with a base of the at least one sensor.

In the preferred embodiment of the disclosure, the analyzing module (116) of the system (100) is configured to analyze performance of the at least one low-cost sensor using the predefined range of values of the soil moisture, the determined percentage of the silver metal pixel and the connectivity of the silver metal pixel with the base. The performance analysis includes evaluation of degradation stages of the low-cost sensor. It is to be noted that the low-cost sensor does not have a high-quality sensing-element. Hence, the low-cost sensor undergoes quick wear and tear and experiences poor performance.

Figure 2:
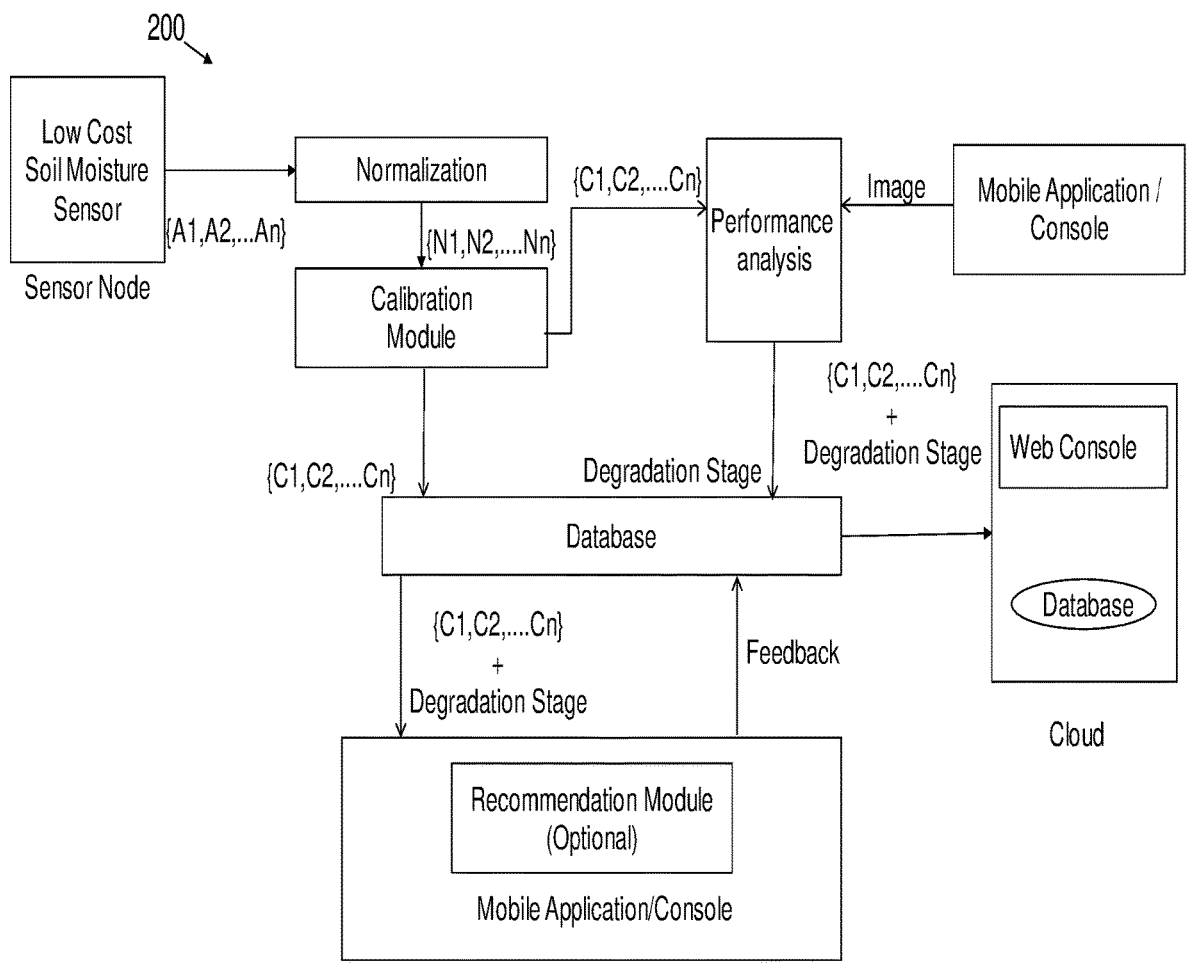
FIG. 2 is a functional block diagram of the system to monitor performance of low-cost sensors used in soil moisture measurement, in accordance with some embodiments of the present disclosure.

Referring FIG. 2, wherein an image of a low-cost sensor is captured and converted to a grayscale and blurred using a bilateral filter in order to remove noise and preserve sharp edges. A predefined Otsu thresholding is applied, and a binary image is obtained. The binary image is used to remove the background of the low-cost sensor image. The binary image is used as a mask in order to replace value of all the pixels that do not belong to the low-cost sensor by 0. Further, the threshold value is used to perform canny edge detection over the low-cost sensor image. Erosion and dilation are performed on the edge-map in order to close gaps between the edges and avoid missing and closed contour.

Further, a contour detection is applied based on a topological structural analysis on the binary edge-map in order to obtain the outer boundary of the low-cost sensor. An ellipse fitting is applied where the contour points are approximated by ellipses using least squares optimization to obtain angle. Once the angle is obtained, a morphological operation of rotation is applied on the sensor pixels in order to get it vertically aligned in the image.

In another aspect, an edge-detected image is used to find hierarchical contours in the image. The hierarchical contours are sorted in descending order of the area and converted to minimum area bounding rectangle. It helps to find common vertices and sides of probes and base, which in turn help to get the relative position and connectivity between them.

In yet another aspect, after localizing the sensor parts, the system identifies a silver metal pixel inside the contour of each probe. For the area inside the detected box of sensor probe, identify the silver metal pixels. All pixels satisfying the hue saturation value (HSV) threshold range for all channels are considered as silver values. Hue—any degree, Saturation—0 to 4%, Value=60 to 85%. After getting the silver pixels, calculate the percentage of pixels in each probe. Apart from metal pixels, the connectivity of the sensing element with the base of sensor is checked. From the first row on the side of probe connected to the base, if there are enough silver pixels connected to base (i.e. $(1/9)*(\text{width of probe})^2$), the sensing element is termed to be connected. Connectivity is also considered along with the quantity of metal pixels for image-based analysis of sensor health.

In the preferred embodiment of the disclosure, the recommendation module (118) of the system (100) is configured to recommend one or more corrective measures for the at least one low-cost sensor based on the performance analysis. The one or more corrective measures include modification in the existing low-cost sensor and replacement of the existing low-cost sensor with a new low-cost sensor. It is to be noted that the performance analysis of the low-cost sensor is done for images of front and backsides of the low-cost sensor clubbed with a mean and median of the moisture values of the low-cost sensor. The percentage error in the moisture values of the sensor at a given moisture level has been used as reference to decide on different degradation levels in the sensor.

Figure 3:
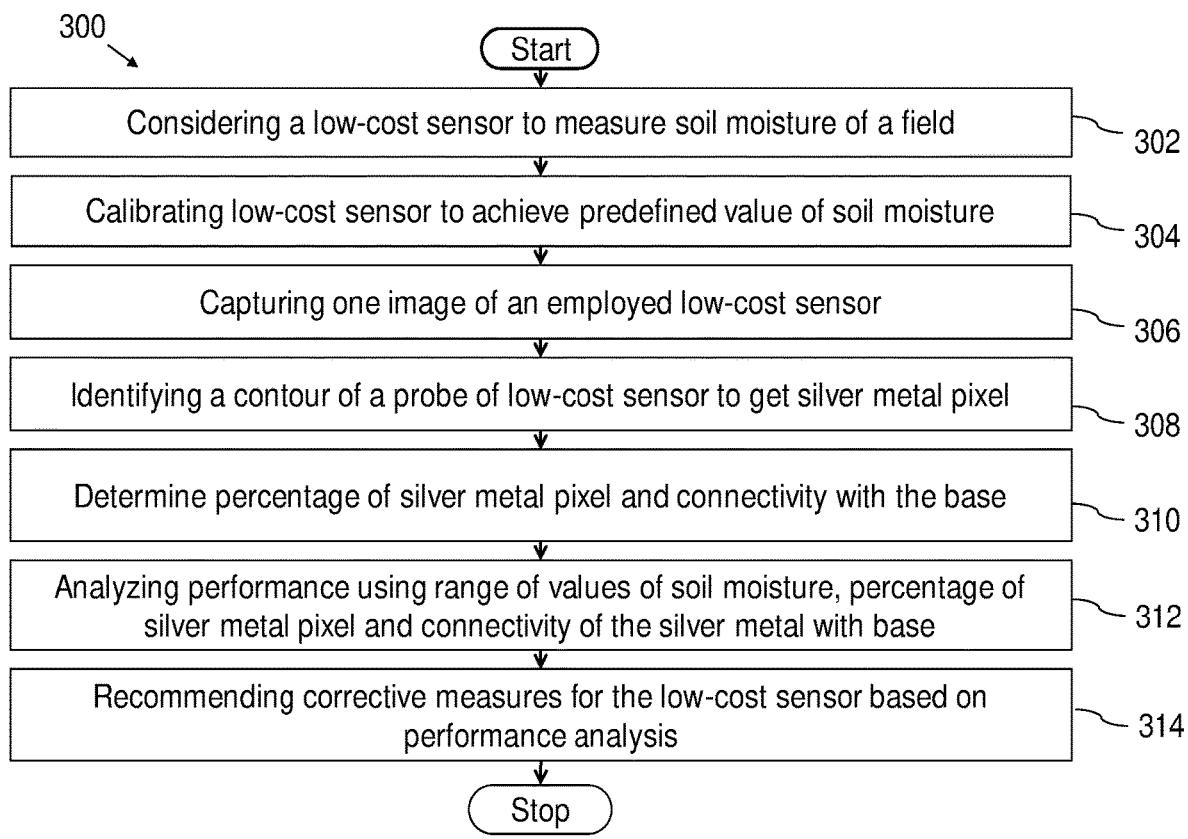
FIG. 3 is a flow diagram to illustrate a method to monitor performance of low-cost sensors used in soil moisture measurement, in accordance with some embodiments of the present disclosure.

Referring FIG. 3, a processor-implemented method (300) to monitor performance of low-cost sensors used in soil moisture measurement. The method comprises one or more steps as follows.

Initially, at the step (302), considering a low-cost sensor to measure soil moisture of a field, wherein the low-cost sensor works on a principle of resistance or capacitance through one or more sensing elements.

In the preferred embodiment of the disclosure, at the next step (304), calibrating the at least one low-cost sensor at a sensor calibration module based on predefined parameters to measure one or more values of the soil moisture.

In the preferred embodiment of the disclosure, at the next step (306), capturing at least one image of the employed at least one low-cost sensor using a multimedia component. The captured at least one image is pre-processed to remove noise and detect a binary edge-map of the at least one captured image. The pre-processing of the at least one image includes conversion of each of one or more images into a greyscale and blur the grey-scaled images using a bilateral filter.

In the preferred embodiment of the disclosure, at the next step (308), identifying a contour of a probe of the at least one low-cost sensor from the pre-processed at least one image based on a topological structural analysis on the binary edge-map of the image. The identified contour of the probe provides a silver metal pixel of each probe.

In the preferred embodiment of the disclosure, at the next step (310), determine a percentage of the silver metal pixel and a connectivity of the silver metal pixel with a base of the at least one sensor.

In the preferred embodiment of the disclosure, at the next step (312), analyzing a performance of the at least one low-cost sensor using the predefined range of values of the soil moisture, the determined percentage of the silver metal pixel and the connectivity of the silver metal pixel with the base. The performance analysis includes evaluation of degradation stages of the low-cost sensor.

In the preferred embodiment of the disclosure, at the last step (314), recommending one or more corrective measures for the at least one low-cost sensor based on performance analysis of the at least one low-cost sensor. The one or more corrective measures include modification in the existing low-cost sensor and replacement of the existing low-cost sensor with a new low-cost sensor.

Figure 4:
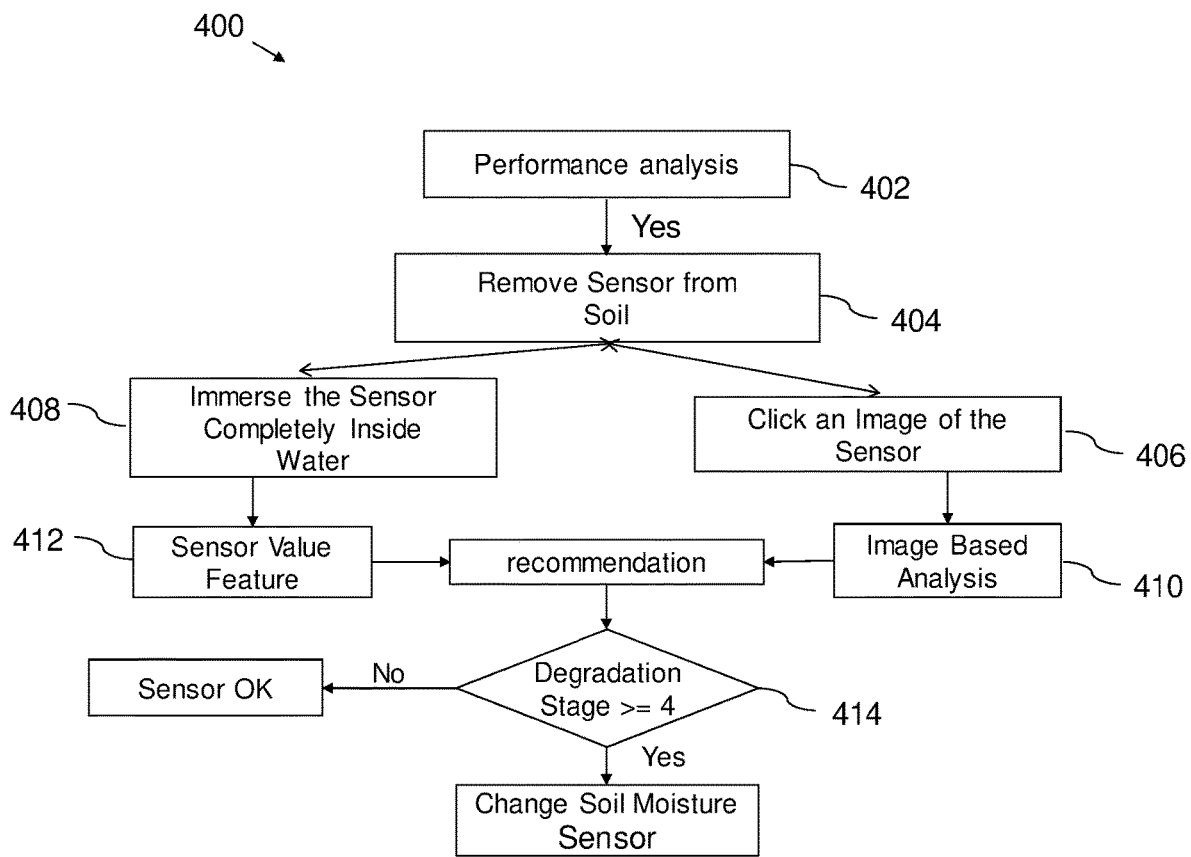
FIG. 4 is a schematic diagram to monitor performance of low-cost sensors used in soil moisture measurement, in accordance with some embodiments of the present disclosure.

Referring FIG. 4, a schematic flow diagram (400) to illustrate performance monitoring, wherein a low-cost sensor is calibrated based on behavior of a rugged sensor as it is trained to recognize conditions ranging from dry to moist to extreme wet conditions. Further, the low-cost sensor is calibrated to learn the behavior of a known rugged sensor and to de-noise response of low-cost sensors to derive stable measurements similar to the expensive rugged sensors. Herein, the steps are being incorporated to monitor performance of the low-cost sensors and recommend modifications within the existing low-cost sensors or replacement with a new low-cost sensor. At step (402), the performance analysis of low-cost sensor is initiated. At step (404) the sensor is removed from the soil, and at step (406) an image is clicked of the removed low-cost sensor. Further, at step (408) the low-cost sensor is immersed completely inside water and at step (410) the image is analyzed based on the sensor value features obtained at step (412). Further, to recommend corrective measure based on the performance of the sensor at step (414) based on the evaluation of degradation stages. It would be appreciated that if the degradation stage is greater and equal then 4 then the low-cost sensor is replaced with new low-cost sensor.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address unresolved problem associated with monitoring performance of a low-cost sensor used for soil moisture measurement. Low-cost sensors available in the market usually have shorter lifetimes due to faster wear and tear of the sensing element. The low-cost sensors often give out the raw measurements that are a function of the both the medium and the quality of the sensing element in contact with the medium. There is no derived parameter for irrigation as such. Once the low-cost sensors are deployed in the farm, wear and tear of the sensing element is not observed or most of the times goes unnoticed. It leads to logging of incorrect sensor values and therefore incorrect estimates.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device, which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development would change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

The invention claimed is:

1. A system comprising:
   at least one memory storing a plurality of instructions;
   one or more hardware processors communicably coupled with the at least one memory, wherein the one or more hardware processors are configured to execute one or more modules;
   at least one first sensor configured to measure soil moisture of a field, wherein the first sensor works on a principle of resistance or capacitance through a sensing element;
   a calibration module configured to calibrate the first sensor based on a set of predefined parameters to achieve a predefined value of the soil moisture, wherein the calibrated first sensor is employed in the field to measure soil moisture;
   a multimedia component configured to capture at least one image of the first sensor, wherein the captured at least one image is pre-processed to remove noise and detect a binary edge-map of the at least one captured image;
   an identification module configured to identify a contour of a probe of the first sensor from the pre-processed at least one image based on a topological structural analysis on the binary edge-map of the image, wherein the identified contour of the probe provides a silver metal pixel of the probe and wherein all pixels satisfying hue saturation value (HSV) threshold range for all channels are considered as silver values, and value of Hue in the HSV being any degree, value of saturation in the HSV ranges from 0% to 4% and value in the HSV ranges from 60% to 85%;
   a determining module configured to determine a percentage of the silver metal pixel and a connectivity of the silver metal pixel with a base of the first sensor;
   an analyzing module configured to analyze performance of the first sensor using a predefined range of values of the soil moisture, the determined percentage of the silver metal pixel and the connectivity of the silver metal pixel with the base and an evaluation of degradation stages of the first sensor; and
   a recommendation module configured to recommend one or more corrective measures for the first sensor based on the performance analysis, wherein the one or more corrective measures include modification in the first sensor or replacement of the first sensor with a new sensor.

2. The system of claim 1, wherein the pre-processing of the one or more image includes conversion of each of one or more images into a greyscale images and blurring the grey-scaled images using a bilateral filter.

3. The system of claim 1, wherein the calibration of the first sensor includes normalization of incoming values from the first sensor based on predefined values determined through a second sensor.

4. The system of claim 3, wherein the normalization of incoming values involves finding a minimum value and a maximum value of the soil moisture.

5. The system of claim 3, wherein the normalization is a process of mapping of raw values, which changes even between the sensing elements of the same family to a percentage value based on air and water measurement.

6. A processor-implemented method comprising:
   selecting, via one or more hardware processors, a first sensor to measure soil moisture of a field, wherein the first sensor works on a principle of resistance or capacitance through its sensing element;
   calibrating, via the one or more hardware processors, the first sensor based on predefined parameters to achieve a predefined value of the soil moisture, wherein the calibrated first sensor is employed in the field to measure soil moisture;
   capturing, via the one or more hardware processors, at least one image of the first sensor using a multimedia component, wherein the captured at least one image is pre-processed to remove noise and detect a binary edge-map of the at least one captured image;
   identifying, via the one or more hardware processors, a contour of a probe of the first sensor from the pre-processed at least one image based on a topological structural analysis on the binary edge-map of the image, wherein the identified contour of the probe provides a silver metal pixel of each probe and wherein all pixels satisfying hue saturation value (HSV) threshold range for all channels are considered as silver values, and value of Hue in the HSV being any degree, value of saturation in the HSV ranges from 0% to 4% and value in the HSV ranges from 60% to 85%;
   determining, via the one or more hardware processors, a percentage of the silver metal pixel and a connectivity of the silver metal pixel with a base of the first sensor;
   analyzing, via the one or more hardware processors, a performance of the first sensor using a predefined range of values of the soil moisture, the determined percentage of the silver metal pixel and the connectivity of the silver metal pixel with the base and an evaluation of degradation stages of the first sensor; and
   recommending, via the one or more hardware processors, one or more corrective measures for the first sensor based on the performance analysis, wherein the one or more corrective measures include modification in the first sensor or replacement of the first sensor with a new sensor.

7. The processor-implemented method of claim 6, wherein the pre-processing of the at least one image includes conversion of each of one or more images into a greyscale and blur the grey-scaled images using a bilateral filter.

8. The processor-implemented method of claim 6, wherein the calibration of the first sensor includes normalization of incoming values from the first sensor based on predefined values determined through a second sensor.

9. The processor-implemented method of claim 8, wherein the normalization involves finding a minimum value and a maximum value of the soil moisture.

10. The processor-implemented method of claim 6, wherein the normalization is a process of mapping of raw values, which changes even between the sensing elements of the same family to a percentage value based on air and water measurement.

11. A non-transitory computer readable medium storing one or more instructions which when executed by a processor on a system, cause the processor to perform a method comprising:

selecting, via one or more hardware processors, a first sensor to measure soil moisture of a field, wherein the first sensor works on a principle of resistance or capacitance through its sensing element;

calibrating, via the one or more hardware processors, the first sensor based on predefined parameters to achieve a predefined value of the soil moisture, wherein the calibrated first sensor is employed in the field to measure soil moisture;

capturing, via the one or more hardware processors, at least one image of the first sensor using a multimedia component, wherein the captured at least one image is pre-processed to remove noise and detect a binary edge-map of the at least one captured image;

identifying, via the one or more hardware processors, a contour of a probe of the first sensor from the pre-processed at least one image based on a topological structural analysis on the binary edge-map of the image, wherein the identified contour of the probe provides a silver metal pixel of each probe and wherein all pixels satisfying hue saturation value (HSV) threshold range for all channels are considered as silver values, and value of Hue in the HSV being any degree, value of saturation in the HSV ranges from 0% to 4%, and value in the HSV ranges from 60% to 85%;

determine, via the one or more hardware processors, a percentage of the silver metal pixel and a connectivity of the silver metal pixel with a base of the first sensor;

analyzing, via the one or more hardware processors, a performance of the first sensor using a predefined range of values of the soil moisture, the determined percentage of the silver metal pixel and the connectivity of the silver metal pixel with the base and an evaluation of degradation stages of the first sensor; and recommending, via the one or more hardware processors, one or more corrective measures for the first sensor based on the performance analysis, wherein the one or more corrective measures include modification in the first sensor or replacement of the first sensor with a new sensor.

* * * * *